US006471716B1

(12) United States Patent
Pecukonis

(10) Patent No.: US 6,471,716 B1
(45) Date of Patent: Oct. 29, 2002

(54) LOW LEVEL LIGHT THERAPY METHOD AND APPARATUS WITH IMPROVED WAVELENGTH, TEMPERATURE AND VOLTAGE CONTROL

(76) Inventor: Joseph P. Pecukonis, 7505 S. Cove Cir., Littleton, CO (US) 80122

( * ) Notice: Subject to any disclaimer, the term of this patent is extended or adjusted under 35 U.S.C. 154(b) by 7 days.

(21) Appl. No.: 09/613,848

(22) Filed: Jul. 11, 2000

(51) Int. Cl.⁷ ............................................. A61N 5/067
(52) U.S. Cl. ............................... 607/89; 606/9; 606/11
(58) Field of Search ..................... 606/1–19; 607/88–89

(56) References Cited

U.S. PATENT DOCUMENTS

| | | | | |
|---|---|---|---|---|
| 4,585,002 A | * | 4/1986 | Kissin | 607/96 |
| 4,646,743 A | | 3/1987 | Parris | |
| 4,852,549 A | * | 8/1989 | Mori | 607/92 |
| 4,905,690 A | | 3/1990 | Ohshiro et al. | |
| 4,930,504 A | | 6/1990 | Diamantopoulos et al. | |
| 5,259,380 A | | 11/1993 | Mendes et al. | |
| 5,344,434 A | | 9/1994 | Talmore | |
| 5,358,503 A | | 10/1994 | Bertwell et al. | |
| 5,406,172 A | * | 4/1995 | Bennett | 315/112 |
| 5,500,009 A | | 3/1996 | Mendes et al. | |
| 5,604,757 A | * | 2/1997 | Liang et al. | 372/29 |
| 5,616,140 A | * | 4/1997 | Prescott | 606/10 |
| 5,634,711 A | * | 6/1997 | Kennedy et al. | 315/224 |
| 5,640,978 A | * | 6/1997 | Wong | 128/898 |
| 5,698,866 A | * | 12/1997 | Doiron et al. | 257/99 |
| 5,749,868 A | | 5/1998 | Furumoto | |
| 5,885,274 A | | 3/1999 | Fullmer et al. | |
| 5,944,748 A | * | 8/1999 | Mager et al. | 607/88 |
| 5,989,245 A | * | 11/1999 | Prescott | 606/14 |
| 5,998,977 A | * | 12/1999 | Hsu et al. | 324/272 |
| 6,063,108 A | * | 5/2000 | Salansky et al. | 607/89 |
| 6,100,677 A | * | 8/2000 | Farrenkopf | 323/285 |
| 6,156,028 A | * | 12/2000 | Prescott | 606/2 |
| 6,214,033 B1 | * | 4/2001 | Ii et al. | 604/20 |
| 6,221,095 B1 | * | 4/2001 | Van Zuylen et al. | 607/88 |
| 6,358,272 B1 | * | 3/2002 | Wilden | 606/13 |
| 6,366,802 B1 | * | 4/2002 | Haber et al. | 600/474 |

OTHER PUBLICATIONS

Laser Therapy, Kenji Asada, et al., Clinical Application of GaAIAs 830 nm Diode Laser in Treatment of Rheumatoid Arthritis, 1991, vol. 3, pp. 77–81.
T. Burns, et al., Killing of Bacteria by Low Poer Laser Light, Jul. 3, 1997.
Radiation Lab, Background for Infrared Radiation and Temperature, Mar. 12, 1999, 6 pages.
Spectra–Medics Pty Ltd, Low–Level Laser Therapy, A Concise Guide for Practising Therapists, Dec. 17, 1998, 15 pages.

(List continued on next page.)

Primary Examiner—John P. Leubecker
Assistant Examiner—Henry M. Johnson
(74) Attorney, Agent, or Firm—John R. Ley; L. Jon Lindsay

(57) ABSTRACT

A photo-therapy device emits photo-therapeutic radiation to treat. living tissue. The device incorporates an array of emitters, the photo emissions of which is dependent on their temperature. Temperature feedback is provided to a voltage supply that supplies current to the emitters, to regulate the voltage supply level and the temperature of the emitters. Additionally, the wavelength of the radiation is dependent on the temperature of the emitters, so the wavelength is moved closer to an optimum wavelength for absorption by the tissue by controlling the temperature of the emitters. Furthermore, the useful life of the emitters is extended by pulsing the emitters on and off by sequentially applying an activation signal to one group of emitters at a time. Also, the device can operate on a wide range of voltage input levels since it utilizes a switching regulator, which can convert a voltage level in the range to the level required to drive the array of emitters. The photo-therapeutic infrared light may be used to treat insect bites and to relieve headaches in human beings. The infrared light emitters may be incorporated into a mouthpiece for treating gum tissues.

41 Claims, 4 Drawing Sheets

OTHER PUBLICATIONS

AGNIS, Valentinas Murauskas, Low Intensity Laser Therapy equipment, Laser therapy: energetic or informational effect?, Dec. 17, 1998, 8 pages.

Equine Therapy Product Information, Pain–X–2000 What is Low Level Light Therapy?, Dec. 17, 1998, 2 pages.

SBRC: Infrared Radiation, Infrared Radiation, Mar. 12, 1999, 4 pages.

iQVC Shop Product Detail page, Ultra Infrared Pain Reliever & Massager w/ Attachments, Dec. 9, 1998, 1 page.

Omega Laser Products, Products Guide, Dec. 17, 1998, 3 pages.

LASERMED Ltd.—Medical Laser Center, Medical Treatments, Dec. 17, 1998, 2 pages.

University of Delaware, Welcome to Lasers and Physical Therapy Care, Nov. 16, 1997, 7 pages.

MAXIM Integrated Products, 12V or Adjustable, High Efficiency, Low IQ, Set–Up DC–DC Controller, Jul., 1995, 16 pages.

National Semiconductor Corporation, LMC555 CMOS Timer, May, 1997, 8 pages.

ZETEC Semiconductors, N–Channel Enhancement Mode Vertical DMOS FET, Issue 2, Mar. 1994, 3 pages.

Motorola, Inc., Product Preview TMOS E–FET Power Field Effect Transistor N–Channel Enhancement–Mode Silicon Gate, 1998, 4 pages.

Hewlett Packard, High–Performance IR Emitter and IR PIN Photodiode in Subminiature SMT Package, Undated, 10 pages.

National Semiconductor Corporation, LP2950/A–XX and LP2951/A–XX Series of Adjustable Micropower Voltage Regulators, Jun., 1997, 5 pages.

Hewlett Packard, Long Term Reliability Data for AlInGaP Technology T–1 3/4 LED Lamps, Jul., 1998, 4 pages.

Hewlett Packard, Pulsed Operating Ranges for AlInGaP LEDs vs. Projected Long Term Light Output Performance, Feb., 1998, 6 pages.

Hewlett Packard, Projection of Long Term Light Output Performance for AS AlInGaP LED Technology, Apr., 1996, 2 pages.

Hewlett Packard, Projected Long Term HTOL Light Output Degradation of Precision Optical Performance AlInGaP LEDs, Nov., 1998, 2 pages.

Hewlett Packard, Temperature Compensation Circuit for Constant LED Intensity, May, 1995, 2 pages.

* cited by examiner

LOW LEVEL LIGHT THERAPY METHOD AND APPARATUS WITH IMPROVED WAVELENGTH, TEMPERATURE AND VOLTAGE CONTROL

This invention relates to photo-therapy or low level light therapy (LLLT) used is to stimulate natural healing functions. More particularly, the present invention relates to a new and improved method and device for delivering therapeutic light energy, preferably non-coherent infrared light, which makes use of relatively inexpensive light emitters that are controlled to increase the amount of light energy absorbed by the tissue while still increasing the useable longevity of the emitters under a variety of different portable and use conditions.

BACKGROUND OF THE INVENTION

Photo-therapy is the application of light energy to biological tissue for the purpose of stimulating certain biological functions, such as natural tissue healing and regrowth processes. Alternatively, a higher power level of photo-therapy may inhibit natural biological functions of the tissue or destroy the tissue, as may be applied in the case of cancerous tissue.

The exact nature of the benefits or effects of photo-therapy on the tissue are not known with certainty. However, many studies have shown that a low level of light and/or heat radiation on tissue is associated with enhanced tissue healing.

Therapists have used photo-therapy to treat a variety of illnesses, injuries and conditions. For example, photo-therapy has been used to treat soft tissue injuries such as capsulitis, bursitis, sprains, strains, hematomas and tendinitis; acute and chronic joint problems such as osteoarthritis, rheumatoid arthritis, and ligament and tendon injuries; chronic pain such as post herpetic neuralgia, chronic back and neck pain, metatarsalgia, trigeminal neuralgia, brachial neuralgia, plantar fisciitis, frozen shoulder and carpal tunnel syndrome. Photo-therapy has also been used to treat non-union and small bone fractures, among other things. Photo-therapy has been used to treat herpes, apthous ulcers, leg ulcers, dermatitis, wound healing, burns, acute epididymitis, otorhinolargngology, gynecology, obstetrics, superficial AP stimulation and tonification, cosmetic imperfections and acne, among other things.

Generally, photo-therapy is accomplished by radiating light energy into a patient's tissue at or below the skin or surface of the tissue. The radiation is applied at wavelengths either in the visible range or the invisible infrared (IR) range by placing the light source in close proximity to, even touching, the patient's skin. Photo-therapy may also be accomplished by applying coherent and non-coherent light energy, lased and non-lased light energy, and narrow and broadband light energy, in either a continuous or pulsed manner. The radiation energy is also typically applied at a low power intensity, typically measured in milliwatts. The relatively low radiation energy applied in therapy is called low level light therapy (LLLT).

Visible light radiation typically provides therapeutic effects at the surface of the tissue, i.e. at the skin. IR radiation has a wavelength that penetrates through the skin to achieve deeper therapeutic effects on subcutaneous and deeper tissue. The depth of the therapeutic effect has to do with the absorptivity of the tissue to which the radiation is applied. Deep tissue include substantial water but the skin is relatively dry. The absorptivity characteristic of water peaks at radiation wavelengths of about 900 nm. IR radiation in range of wavelengths from 760–1260 nms penetrates into the deeper sub-dermal tissue. Deeper tissue treatment is useful for healing musculoskeletal injuries, for sports therapy, for reaching deeper acupuncture and myofascial trigger points, and for healing deep wounds, among other things.

Since 900 nm wavelength radiation achieves maximum penetration into most tissue, it is advantageous to supply IR radiation at or near a 900 nm wavelength. Light sources that emit radiation near a 900 nm wavelength are lasers, and lasers are expensive and/or difficult to operate. Examples of radiation emitting sources operative at a 900 nm wavelength include helium neon (HeNe) lasers, alexandrite, titanium sapphire, chromium doped fluoride lasers, and semiconductor diode lasers. The relatively high expense of these types of lasers makes it economically feasible to incorporate only a single one, or a few, of such radiation sources in a photo-therapeutic device. With the reduced number of light emitting sources, the effective treatment area may become substantially limited to a relatively small area.

Other types of radiation light sources such as conventional non-coherent IR light emitting diodes (LEDs) may be employed, but the radiation emitted from such devices typically falls well outside of the peak absorptivity range for water. Using such light source devices achieves less-than-optimal energy penetration and absorption within the tissue. Gallium aluminum arsenide (GaAlAs) LEDs have a room temperature radiation wavelength of approximately 880 nm. Even though this radiation wavelength is closer to the 900 nm peak absorptivity wavelength for water, it is still not optimum for maximum energy absorption. Furthermore, GaAlAs LEDs are more expensive than other types of non-coherent IR LEDs, thus adding a cost consideration to the overall price of the photo-therapy device. In addition, non-coherent IR LEDs are prone to burn out after prolonged periods of continuous use.

One approach to avoiding premature failure resulting from long time periods of continuous use of non-coherent IR LEDs in photo-therapy devices is to pulse the IR LEDs on and off. Pulsing at a predetermined duty cycle adds to the useful longevity of the device because it is only energized on a part-time basis. Pulsing increases the useful life of the device, thereby somewhat offsetting the high cost of the light emitting devices.

One problem with pulsing the photo-radiation sources, particularly a large array of IR LED sources, is that the entire array is turned on and off at the same time, causing substantially large changes in the amount of current conducted by the IR LED sources during the on time period compared to the time periods when the LED sources are nonconductive. The circuit elements necessary to create and sustain such current differentials are themselves large and expensive.

The current conducted by the IR LED sources causes them to heat. The wavelength of the IR radiation emitted is related to the temperature of the LEDs. If the temperature of the LEDs can be controlled, the operating wavelength of energy emitted can be controlled. More precisely controlling the wavelength of the emitted energy can enhance the effectiveness of the treatment. However, thermal instability of many IR sources makes it difficult or impossible to control the effectiveness of the wavelength of the emitted radiation.

Another disadvantage of many photo-therapy devices is the inability of the devices to operate on a wide range of voltage inputs. This restriction prevents photo-therapy and LLLT devices from being portable and convenient to use, since they must generally be connected to a conventional commercial AC mains power supply. This power supply restriction effectively limits the photo-therapy and LLLT devices for use only at home or in a treatment facility, where a ready source of AC power is available. Thus, most existing photo-therapy or LLLT devices cannot be used in a vehicle to provide treatment for chronic pain when sitting and driving for long periods, or on a sports field to provide immediate treatment for sporting injuries, or by an emergency medical team to provide early treatment to accident victims.

Photo-therapy is sometimes applied conjunctively with heat therapy. A heat source in the photo-therapy device will transfer heat to the surface of the tissue. For deep tissue treatment, surface heating is entirely impractical, since the surface tissue would have to be heated to intolerable temperatures to effectively penetrate to the deeper tissue. The deep penetrating IR wavelengths are preferable for use in deep tissue treatment.

It is with respect to these and other considerations, that the present invention has evolved.

SUMMARY OF THE INVENTION

One aspect of the invention involves a photo-therapy or LLLT device which utilizes relatively low-cost IR LEDs, such as a gallium aluminum arsenide LEDs, which are controlled to cause them to emit radiation at a wavelength which is closer to the 900 nm peak absorptivity characteristic of water. As a result, less expensive radiation emitting sources may be employed to obtain energy penetration benefits comparable to those obtained from considerably more expensive laser sources.

To achieve these and other similar improvements, a photo-therapy device of the present invention includes an emitter, such as an infrared light emitting diode, which emits infrared radiation at a photo-therapeutic wavelength when current is conducted through the emitter. The wavelength of the infrared radiation is related to the temperature of the emitter, and the temperature of the emitter is related to the current conducted through the emitter. A temperature regulation circuit of the device includes a temperature sensor disposed proximate to the emitter to sense the temperature of the emitter. A temperature regulation circuit supplies a control signal related to the temperature of the emitter sensed by the temperature sensor. A controllable power supply is connected to the emitter and responds to the control signal to supply current to the emitter to establish and maintain a predetermined temperature of the emitter to result in the emission of infrared radiation at a predetermined wavelength. In this manner, the wavelength of the emitted radiation is controlled to establish the desired emitted radiation wavelength during the course of the photo-therapy which is closer to the wavelength for optimal energy absorption from the light energy.

Another aspect of the present invention involves pulsing the light emitters to prolong their useful lifetime without creating unacceptable and difficult-to-handle current fluctuations, all of which contributes to simplifying and reducing the cost of the photo-therapy or LLLT device. To achieve these and other improvements, the photo-therapy device includes a plurality of emitters arranged in an array, with the array having groups of at least one emitter per group. One controllable switch is associated with each group, and the controllable switch conducts current through each emitter of the associated group. A selector is connected to each of the controllable switches, and the selector supplies an activation signal to each of the controllable switches to cause each of the controllable switches to become conductive. Each row of emitters as an LED that emits light in the visible spectrum, and thereby serves as an indicator to the user that each row of emitters is working properly. A controllable power supply is connected to the emitters of the array, and it applies a controllable level of output voltage to the array. The level of the output voltage establishes the amount of current flowing through the emitters.

Another aspect of the present invention involves a photo-therapy or LLLT device which is portable and capable of supplying photo-therapy in a variety of different locations and situations other than exclusively at home, in the practitioner's office or in treatment facilities. As well, the radiation may be applied in more convenient conditions, such as while traveling, more quickly following an accidental injury, or while transporting an accident victim to an emergency care facility. To accomplish these and other similar improvements, a boost type switching power, or voltage, supply is included within the photo-therapy device. The power supply applies a voltage to the radiation emitters. The boost type switching power supply includes an inductor electrically connected at one terminal to an input voltage supply, a filter capacitor connected at an other terminal of the inductor, a controllable switch connected at the other terminal of the inductor to conduct current through the inductor from the input voltage supply, and a switching regulator connected to the controllable switch. The switching regulator controls a conduction time and a non-conduction time of the controllable switch in response to the output voltage and the current conducted through the inductor. The amount of output voltage from the boost type power supply is directly related to the conduction time of the controllable switch, relative to the non-conduction time of the controllable switch. Adequate power for the photo-therapy devices thereby derived from a wide range of input voltages because of the functionality of the boost-type power supply.

Other uniquely beneficial aspects of the present invention relate to the application of photo-therapeutic infrared radiation to enhance the natural healing process of tissue which has been bitten by insects such as mosquitoes, and gum tissue and to relieve the pain created by headaches.

A more complete appreciation of the present invention and its scope, and the manner in which it achieves the above noted improvements, can be obtained by reference to the following detailed description of presently preferred embodiments of the invention taken in connection with the accompanying drawings, which are briefly summarized below, and the appended claims.

DETAILED DESCRIPTION

A photo-therapy or low-level light therapy (LLLT) device 10 which incorporates the present invention is shown in FIG.

Figure 1:
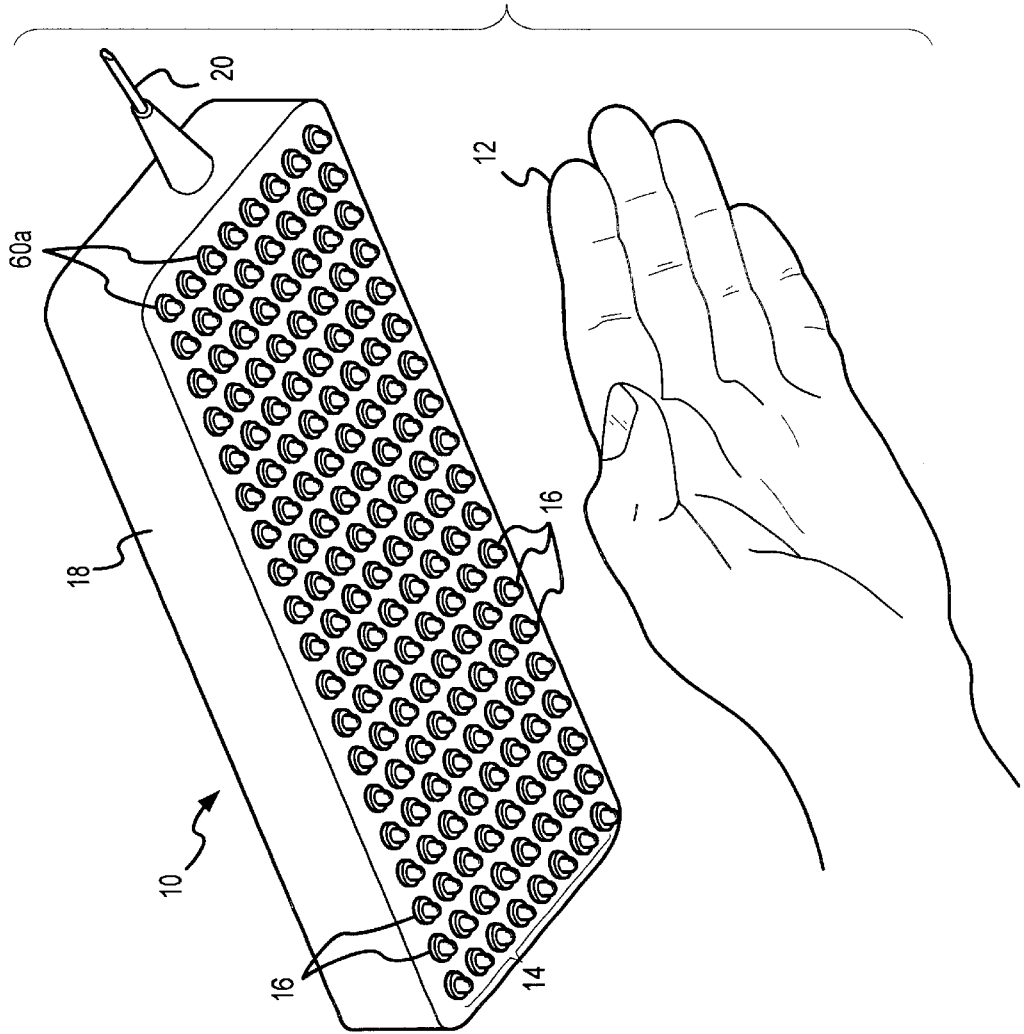
FIG. 1 is a perspective view of a photo-therapy or LLLT device incorporating the present invention, shown applying radiation therapy to tissue.

1. The device 10 is used in providing light therapy treatment to tissue 12 of a patient (not otherwise shown). The device 10 includes an array 14 of photo-therapy radiation emitters, typically gallium arsenide (GaAlAs) infrared (IR) light emitting diodes (LEDs) 16. The GaAlAs IR LEDs 16 are mounted on a housing 18 of the device 10. The LEDs 16 may extend from the housing 18, as shown in FIG. 1, or the LEDs may be positioned in recesses formed in the housing and covered with a transparent label or cover, as is not shown. An electrical power cord 20 extends from the housing 18 to connect the device 10 to an external power source (not shown), such as a commercial AC mains power outlet, an AC/DC converter, a battery pack, an automobile cigarette lighter type outlet, or other power source.

The photo-therapy or LLLT device 10 is used by placing it near or in contact with the tissue 12. When energized, photo-therapeutic radiation energy is delivered from the LEDs 16 and is absorbed by the tissue 12, causing a therapeutic effect. A therapeutic practitioner may use the device 10, or person undergoing treatment may apply the device 10 to his or her own tissue, to accomplish the photo-therapeutic treatment. The device 10 may be placed in a stationary position above the tissue to be treated, or the device 10 may be moved over the tissue to distribute the emitted radiation energy over a larger surface area of tissue than that which would be encountered by stationarily positioning the device 10.

Figure 2A:
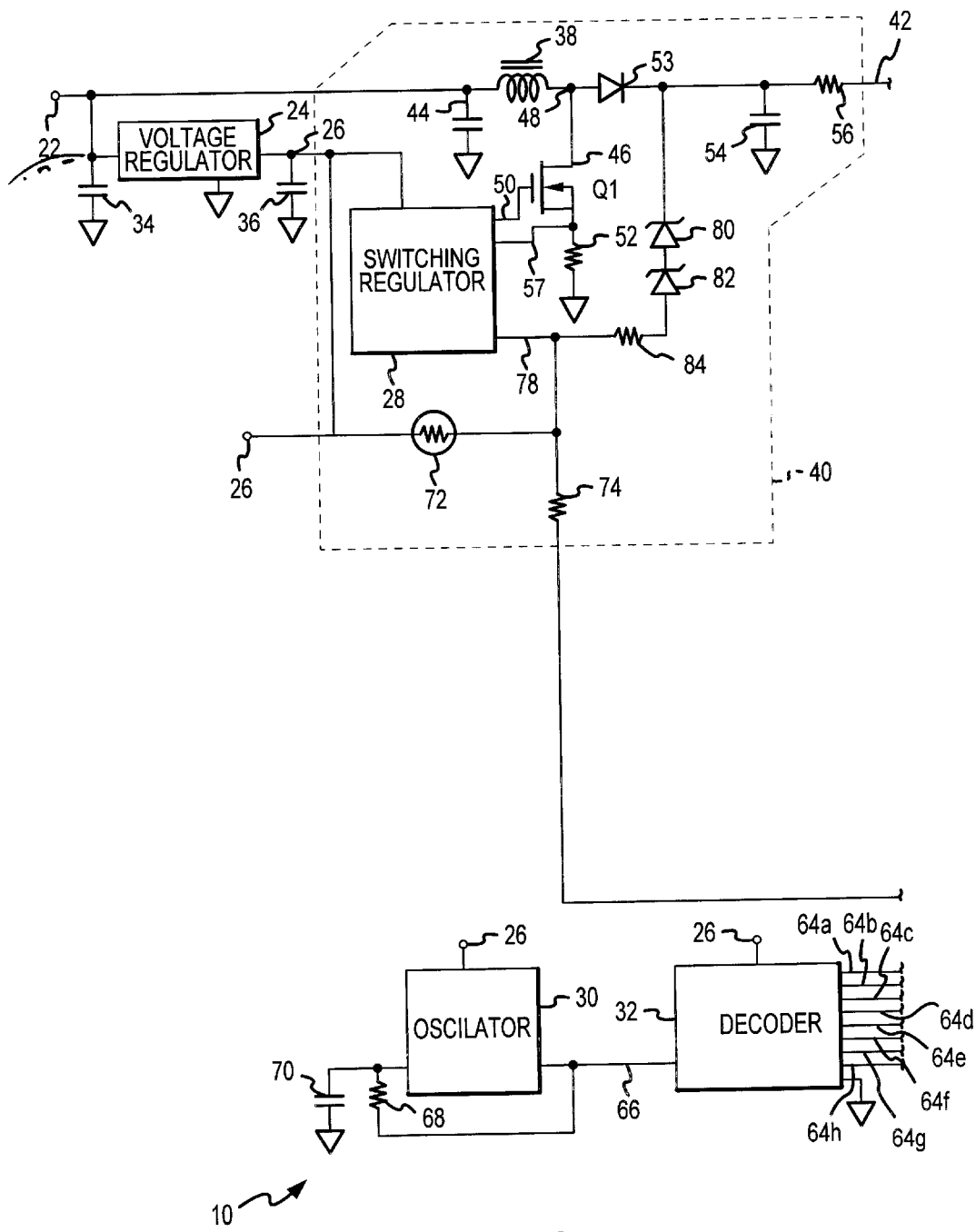
FIGS. 2A and 2B form a single schematic diagram of electrical components of the photo-therapy or LLLT device shown in FIG. 1.
Figure 2B:
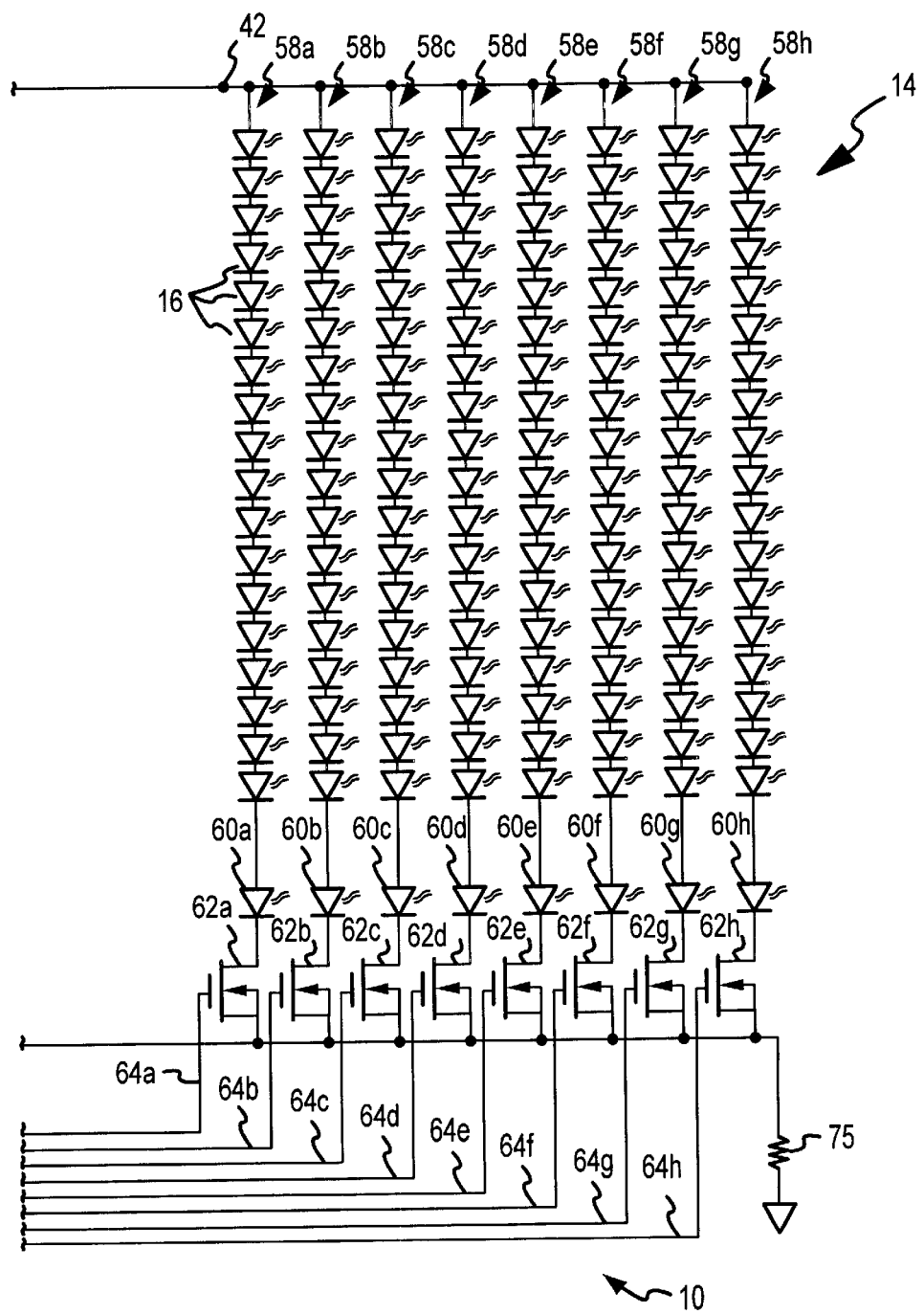

Details concerning the major electronic components of the device 10 are described in conjunction with FIGS. 2A and 2B. Electrical power from the cord 20 is applied to the device 10 at node 22. A conventional linear voltage regulator 24 is connected to the node 22 and delivers regulated operating voltage and power for certain electronic components of the device 10. The linear voltage regulator 24 receives the input voltage at 22 and regulates the input voltage level at 26 to a constant regulated internal working voltage. The regulated voltage at 26 is applied to a conventional switching regulator 28, a conventional oscillator 30 and a conventional decoder 32. Capacitors 34 and 36 are connected at 22 and 26 to the input and the output terminals of the voltage regulator 24 at 22 and 26 for the purpose of smoothing the input and output voltages from the linear voltage regulator 24, respectively.

The input voltage at node 22 is also supplied to an inductor 38. The inductor 38 and the switching regulator 28 form the principal elements of an array power supply 40 for delivering voltage and current to the array 14 of LEDs 16 at node 42. The voltage level at node 42 is regulated to control the characteristics of the radiation emission from the LEDs 16, as discussed below.

The array power supply 40 functions primarily as a boost type switching power supply, in which the inductor 38 functions as a swinging choke inductor. A filter capacitor 44 is connected to the node 22 to filter input voltage excursions applied to the inductor 38. A power switching transistor 46 is connected to an output terminal 48 of the inductor 38. A switching signal at 50 is applied from the switching regulator 28 to the gate of the transistor 46. The switching signal 50 causes the transistor 46 to conduct when the switching signal 50 is asserted, for example at a high level, and the switching transistor 46 becomes nonconductive or cut off when the switching signal 50 is not asserted, for example at a low level. The switching signal 50 is supplied by the switching regulator 28. When the power transistor 46 is conductive, current flows through the inductor 38 to ground through the transistor 46 and a voltage, or current, sensing resistor 52. The current flowing through the inductor 38 charges the inductor 38 with energy. When the switching signal 50 from the switching regulator 28 changes states, the transistor 46 becomes nonconductive, and the energy stored in the inductor 38 is transferred through a diode 53 and is stored in a filter capacitor 54 in the form of a boosted voltage. Current from the filter capacitor 54 flows through a resistor 56 to the node 42 where it is delivered to the array 14 of LEDs 16. The diode 53 rectifies the output signal from the inductor 38 and prevents any reverse current flow from the filter capacitor 54 to the node 22.

The amount of voltage present across the filter capacitor 54 is governed primarily by the amount of energy stored in the inductor 38 during each switching signal 50. For a greater ratio of the assertion (on-time) to the non-assertion (off-time) of the switching signal 50, and its corresponding effect on the switching transistor 46, a larger amount of energy will be stored in the inductor 38. Greater stored energy in the inductor 38 results in a higher voltage at capacitor 54. Conversely, a lesser storage of energy in the inductor 38 results in a diminished voltage level across the capacitor 54. Increasing the ratio of the assertion (on-time) to the non-assertion (off-time) of the switching signal 50 therefore increases the voltage at the capacitor 54, while decreasing this ratio decreases the voltage at the capacitor 54.

When the power transistor 46 is conductive, current flows through the inductor 38, the transistor 46 and the resistor 52. The resistor 52 functions as a voltage or current sensing resistor and provides a current sense signal at 57 to the switching regulator 28. The current sense signal at 57 represents the current flow through the inductor 38. The switching regulator 28 response to the current sense signal 57 to determine when the current flow in the inductor 38 it at or is approaching a saturation level. When the current to the inductor 38 reaches a saturation level, further current flow through the inductor will result in a considerably-diminished increase in energy stored in the inductor 38. At the current saturation point, or some point prior to reaching current saturation, the switching regulator 28 changes the state of the switching signal 50 to terminate conduction of the power transistor 46, causing the current in the inductor 38 to discharge through the diode 53 and charge the filter capacitor 54.

Current from the array power supply 40 delivered at node 42 flows to the LEDs 16 of the array 14, which in the embodiment shown, are arranged in eight parallel vertical groups or columns 58a, 58b, 58c, 58d, 58e, 58f, 58g and 58h. Each column includes number or plurality, e.g. eighteen, of LEDs 16 connected in series to provide the photo-therapy radiation. A single visible-spectrum colored LED 60a, 60b, 60c, 60d, 60e, 60f, 60g and 60h, is connected in series with the photo-therapy LEDs 16 in each of the columns 58a, 58b, 58c, 58d, 58e, 58f, 58g and 58h, respectively. Each of the visible spectrum colored LEDs 60a, 60b, 60c, 60d, 60e, 60f, 60g and 60h functions as an indicator LED 60 to indicate that current is flowing through the LEDs of the column with which it is associated. Other sizes and shapes of arrays 14 may be used. Greater or fewer LEDs 16 may also be incorporated in the array 14 and in the columns of the array 14.

Current flows through the series-connected photo-therapy LEDs 16 and the indicator LEDs 60a–60h of each column when a column current switching transistor 62a, 62b, 62c, 62d, 62e, 62f, 62g and 62h is conductive. The column switching transistors 62a, 62b, 62c, 62d, 62e, 62f, 62g and 62h are connected in each of the columns 58a, 58b, 58c, 58d, 58e, 58f, 58g and 58h, respectively. The column switching current transistors 62a, 62b, 62c, 62d, 62e, 62f, 62g and 62h are switched on and off under the respective control of activation signals applied at 64a, 64b, 64c, 64d, 64e, 64f, 64g and 64h, respectively, which are supplied by the decoder 32. The gates of each of the column switching transistors 62a–62h are connected separately to separate output terminals of the decoder 32, upon which the activation signals 64a–64h are supplied. High and low levels of the activation signals 64a–64h cause the column switching transistors 62a–62h to which they are applied to be switched on and off, into the conductive and nonconductive states, respectively.

When a column current switching transistor 62a–62h is conductive, the corresponding column of photo-therapy LEDs 16 and the indicator LED 60a–60h of that column are also conductive. If all of the LEDs 16 and the indicator LED of that column 58a–58h are functioning properly, then the LEDs 16 of the conductive column 58a–58h will emit the photo-therapeutic radiation and the indicator LED 60a–60h of that column will emit visible radiation to indicate to the user that the column of photo-therapeutic LEDs 16 is also emitting radiation. If one of the LEDs 16 or the indicator LED 60 is open (burned-out), so that current will no longer flow through the series-connected elements of a column 58a–58h, the indicator LED 60a–60h will not light. Since the photo-therapeutic LEDs 16 do not emit visible wavelength radiation, it would be impossible to determine visibly whether any of the photo-therapeutic LEDs 16 in a column 58a–58h had failed, without the indicator LEDs 60a–60h.

The decoder 32 causes only one of the activation signals 64a–64h to be asserted (at a high level) at one time, while the remaining activation signals 64a–64h are not asserted (kept at a low level). The decoder 32 functions in response to a clock signal 66 supplied from the oscillator 30. The clock signal 66 is a cyclically repeating on-off or high-low signal which has a predetermined regular oscillation frequency established by a resistor 68 and a capacitor 70 of the oscillator 30. The oscillating output clock signal 66 is fed back through resistor 68 and capacitor 70, and the time delay aspects of the resistor 68 and capacitor 70 establish the oscillation frequency. For example, and in the preferred embodiment, the values of the resistor 68 and capacitor may establish the clock signal at an oscillation frequency of 8 kHz.

The decoder 32 is a conventional 1-of-8 decoder which has been set to repeatedly index in a regular repeating order among its output terminals and assert one of the activation signals 64a–64h at a time on the next one of its outputs terminals, in response to each pulse or oscillation cycle of the clock signal 66. Thus, with only one of the activation signals 64a–64h being asserted at a time, only one of the column switching transistors 62a–62h is conductive at a time. With only one column 58a–58h being conductive at a time, the conductive duty cycle of the LEDs of each column will be 1/n×100%, where n is the number of columns. In the embodiment shown in FIGS. 2A and 2B, the duty cycle of conductivity for the LEDs of any column is 12.5%. The decoder 32 may drive the LEDs 16 at any appropriate frequency, but preferably at a frequency which generally corresponds to the thermal relaxation time of the IR diodes.

The duty cycle nature of operation of the LEDs 16 extends their usable lifetime. Since each LED 16 is only energized for a relatively small fraction of the entire time that the device 10 delivers photo-therapeutic radiation, each LED 16 can be expected to experience a significantly longer useful lifetime, compared to LEDs 16 which are continuously energized. Because of the extended lifetime, it is possible to drive the LEDs 16 with a slightly higher current that might otherwise be possible, and still expect reasonable longevity of use. As is discussed below, driving the LEDs 16 with a higher current increases their operating temperature, and thereby causes them to emit radiation at a slightly longer wavelength which is closer to the wavelength for optimum absorptivity of the radiation energy in water and tissue which is composed mostly of water. Furthermore, the LEDs 16 and 60a–60h are switched on and off without the more complex circuitry that would be required to cause a voltage supply to separately drive each column 58a–58h. Instead, the power supply 40 provides a relatively steady DC output voltage which may be substantially independent of the input voltage level at node 22. Additionally, since the array power supply 40 drives only one column 58a–58h of the photo-therapy emission LEDs 16 and the indicator LEDs 60a–60h at a time, instead of all of the LEDs 16 of the array 14 simultaneously, the power output of the voltage supply 32 may be scaled accordingly to provide sufficient power to drive only a fraction of the total LEDs 16. Therefore, the circuitry for the photo-therapy device 16 is considerably simplified and the cost of the device 10 (FIG. 1) is reduced.

To cause the LEDs 16 to operate at longer wavelength than at normal room temperature, a temperature control circuit is formed by the series connection of a thermistor 72 and resistor 74 (FIG. 2A) and another resistor 75 (FIG. 2B). The thermistor 72 and resistors 74 and 75 form a voltage divider, and the junction between the thermistor 72 and the resistor 74 is connected to provide a control signal at 78 to the switching regulator 28. The thermistor 72 is located physically proximate to or in thermal contact with the LEDs 16 to provide a signal generally indicative of the temperature of the LEDs 16. The thermistor 72 has a negative temperature coefficient, so as the thermistor 72 gets hotter, it experiences a characteristic decrease in resistance. With a decrease in resistance of the thermistor 72, the voltage divider resistors 74 and 75 supply an increased value of the control signal 78. The increased value of the control signal 78 causes the switching regulator 28 to decrease the ratio of the on-time to the off-time of the switching signal 50, which in turn, causes the switching transistor 46 to diminish the amount of the on-time compared to the amount of off-time, thereby decreasing the energy storage in the inductor 38. Decreased energy in the inductor 38 decreases the voltage level from the array power supply 40 at the capacitor 54. The decreased voltage at node 42 decreases the voltage across, and power consumed by, the LEDs 16 in each column 58a–58h, thereby reducing the heat generated by the LEDs. Reduced heat generation also reduces the operating temperature of the LEDs 16. Conversely, when the thermistor 72 becomes cooler, it will have an increased resistance, causing the level of the control signal 78 to decrease. The decreased value of the control signal 78 causes the switching regulator 28 to increase the conductive on-time of the switching signal 50 compared to its off-time, thereby increasing the voltage output from the array power supply 40. The increased voltage at the node 42 increases the current flow through each conductive column 58a–58h of LEDs 16, which causes the LEDs 16 to increase in temperature. In this manner, the control signal 78, derived from the voltage divider network formed by the thermistor 72 and resistors 74 and 75, regulates the temperature of the LEDs 16 and stabilizes the operating temperature of those LEDs.

The steady-state operating temperature of the LEDs 16 is established by choosing the values of the resistors 74 and 75 and the resistive, thermal-responsive characteristics of the thermistor 72, relative to the voltage from the voltage regulator 24 at node 26, the voltage from the array power supply 40 at node 42 and the response characteristics of the switching regulator 28. The voltage from the array power supply 40 influences the level of the voltage signal across resistor 75 when one column 58a–58h of LEDs is conductive.

The regulation of the steady-state, stabilized operating temperature of the LEDs 16 is selected to establish a predetermined wavelength of the emitted radiation. For example, GaAlAs IR LEDs 16 of the type HSDL44XX Emitter Series from Hewlett Packard Corporation emit non-coherent, infrared radiation at a wavelength of about 880 nm at about room temperature. Since body tissue is mostly water, the LEDs 16 should emit radiation at a wavelength as close as possible to the optimal photo absorptivity wavelength of water, 900 nm, as possible to achieve optimum energy absorption in the tissue. Although IR emitters which deliver IR radiation near this 900 nm peak absorptivity wavelength of water are available, such IR emitters are generally very expensive, and considerably more so than the more common GaAlAs LEDs 16 of the type noted above. Therefore, for economic reasons, if more modestly priced photo-therapeutic IR-emitting LEDs can be employed, the cost of the device 10 will be diminished. The temperature regulation available from the present invention assists in causing the more modestly-priced LEDs to emit radiation at a wavelength closer to the 900 nm peak absorptivity wavelength. For example, to use LEDs of the type noted, the control signal 78 will cause the temperature of the LEDs 16 to stabilize at a predetermined temperature, higher-than-room temperature, such as about 42 degrees Centigrade. Since the wavelength of emitted radiation is generally related to the temperature of the photo-therapeutic LEDs, an elevated temperature above room temperature moves the operating wavelength closer to the peak absorptivity wavelength of 900 nm.

For the type of GaAlAs LEDs described above, a stabilized operating temperature of 42 degrees Centigrade results in an operating wavelength of the radiation of about 884 nm. The operating wavelength of radiation is thus been raised approximately 4 nm. Since the peak absorptivity characteristics are represented by a graph with a relatively sharp peak, the relatively moderate increase in wavelength results in a significantly enhanced degree of radiation absorption. Thus, relatively inexpensive IR LEDs 16 may be effectively forced to operate at higher than normal wavelengths and closer to the 900 nm peak absorptivity wavelength which is closer to the optimum tissue absorption. Because of the duty cycle nature of pulsing the LEDs 16, the higher operating temperature does not significantly diminish the usable lifetime of the LEDs. And elevated operating temperature of the LEDs may also provide the added benefit of thermal therapy to the tissue as well as photo therapy, when the device 10 (FIG. 1) is used in contact or in close proximity to the tissue.

In addition to the temperature control, the device 10 also includes over voltage protection. The over voltage protection is particularly valuable in responding to a situation where one of the LEDs in a column 58a–58h may have burned out, causing that column not to draw current when the activation signal 64a–64h is applied to the column switching transistor 62a–62h. Under such circumstances, the array power supply 40 must limit the amount of energy transferred from the inductor 38 to the filter capacitor 54. Otherwise, the voltage on the filter capacitor 54 would build to an unacceptably high level so that the voltage applied across the next column of conductive LEDs would cause a high current to flow through that column and possibly burn out an LED in that column.

Over voltage protection is achieved as a result of an another voltage divider formed by two Zener diodes 80 and 82, resistor 84, resistor 74 and resistor 75, as shown in FIGS. 2A and 2B. These elements 80, 82, 84, 74 and 75 are connected in series between the output voltage of the filter capacitor 54 and reference potential. The over-voltage protection voltage divider functions in conjunction with the temperature regulation voltage divider network to adjust the value of the control signal 78 to the switching regulator 28 to prevent a momentarily large increase in voltage output from the array power supply 40 at node 42.

When one of the LED columns 58a–58h does not conduct current in response to an activation signal 64a–64h, no current flows through the resistor 75 during the time period in which that LED column would normally conduct current. Under these circumstances, the control signal 78 will decrease because the current that would normally be conducted by that column through resistor 75 will not generate voltage across resistor 75. With the voltage across resistor 75 being low because of the absence of current from the LED nonconductive column, the control signal 78 decreases, and such a decrease would normally cause the switching regulator 28 to increase the on-time of the switching signal 50 in an attempt to increase the voltage from the array power supply 40. However under these circumstances, the two series-connected Zener diodes 80 and 82 become conductive and limit the decrease in voltage of the control signal 78.

When the two series connected Zener diodes 80 and 82 become conductive, the voltage across capacitor 54 has risen beyond normal operating level. The Zener diodes 80 and 82 will not conduct during normal operation of the power supply 40, when each LED column 58a–58h conducts current in the sequence established by the decoder 32. However, when one of the LED columns 58a–58h is not conductive as a result of one of its LEDs 16 being open (burned out), the voltage across the capacitor 54 rises during the time period that the nonconductive LED column 58a–58h would otherwise conduct. The rising voltage causes the Zener diodes 80 and 82 to become conductive, and the voltage of the control signal 78 increases as a result of the conductive Zener diodes 80 and 82. The increased value of the control signal 78 under these conditions causes the switching regulator 28 to immediately reduce the assertion (on-time) of the switching signal 50, thereby reducing the energy transfer from the inductor 38 into the power supply capacitor 54. The reduce transfer of energy diminishes the voltage from the power supply 40 at the node 42. In this manner, the over-voltage protection prevents the array power supply 40 from supplying a relatively high voltage which might damage the LEDs of the next column which becomes conductive after the conductive interval allotted to the nonconductive column.

When the conductive time interval for the next LED column 58a–58h occurs, the conductive LED column diminishes the voltage across the capacitor 54, causing the Zener diodes 80 and 82 to become nonconductive and permitting the temperature control circuit formed by the thermistor 72 and resistor 74 and 75 to establish normal voltage regulation and temperature regulation operation. The Zener voltage values of the Zener diodes 80 and 82 are selected so that the normal range of current through the resistor 75 causes the temperature regulation circuit (elements 72, 74 and 75) to predominate under normal operating conditions. It is only when one of the LED columns 58a–58h becomes nonconductive that the Zener diodes 80 and 82 become effective to confine control signal 78 to level which diminishes the voltage supplied from the inductor 38 to the capacitor 54 of the power supply 40.

The photo-therapy device 10 achieves several significant advantages and improvements. The temperature regulation thermally stabilizes the performance of the IR LEDs 16 so that the radiation wavelength is known and controllable. The thermal controllability permits the emitted radiation wavelength to be forced closer to the optimum tissue absorption wavelength, permitting the use of IR LEDs that do not ordinarily emit radiation as close to the optimum water-absorptivity wavelength as do other, more expensive IR emitter sources. Moreover, the useful life of the IR LEDs is enhanced by pulsing them with a relatively low duty cycle. Pulsing the IR LEDs also permits the use of a less-expensive voltage supply since the voltage supply itself is not required to drive all of the LEDs 16 in the entire array 14 at the same time. However, effective over-voltage protection is still available from the power supply even when its anticipated load (a LED column 58a–58h) is not connected to the power supply as a result of a burned out element. Another advantage is that the device 10 can operate on a wide range of input voltages since the boost-type array power supply 40 can efficiently convert a wide variety of input voltages into an acceptable range of voltage and power to operate the device 10. As a result the device 10 can utilize a wide range of common power supplies, such as an AC outlet, an AC converter, a battery pack, a vehicle cigarette lighter outlet or other power source. Since the device 10 will operate from a variety of difference power sources, the device can be used in a wide variety of situations or environments, such as a medical practitioner's office or examination room, at an accident site or sports field immediately following an injury, in a vehicle while driving, or in any other convenient situation.

Use of the device 10 has proved particularly beneficial in certain types of new therapeutic treatments for human beings. The infrared light radiation delivered by the LEDs 16 has been found to therapeutically enhance the healing process of the tissue 12 at the location where an insect, such as a mosquito, may have bitten a human being. While no precise scientific or medical studies have been conducted, it is believed that early-applied photo-therapy stimulates the healing process to such an extent that insect bites such as mosquito bites are completely healed in a reduced amount of time.

It has also been found that the infrared light radiation delivered from the LEDs 16 provides relatively effective and quick relief from the pain of a headache in a human being, without pharmacological intervention. To achieve headache relief, the infrared light energy is applied to the tissue at the front of the neck of the human. It is believed that the infrared light energy is absorbed by the blood which flows through the neck and into the head and brain of the human being.

Figure 3:
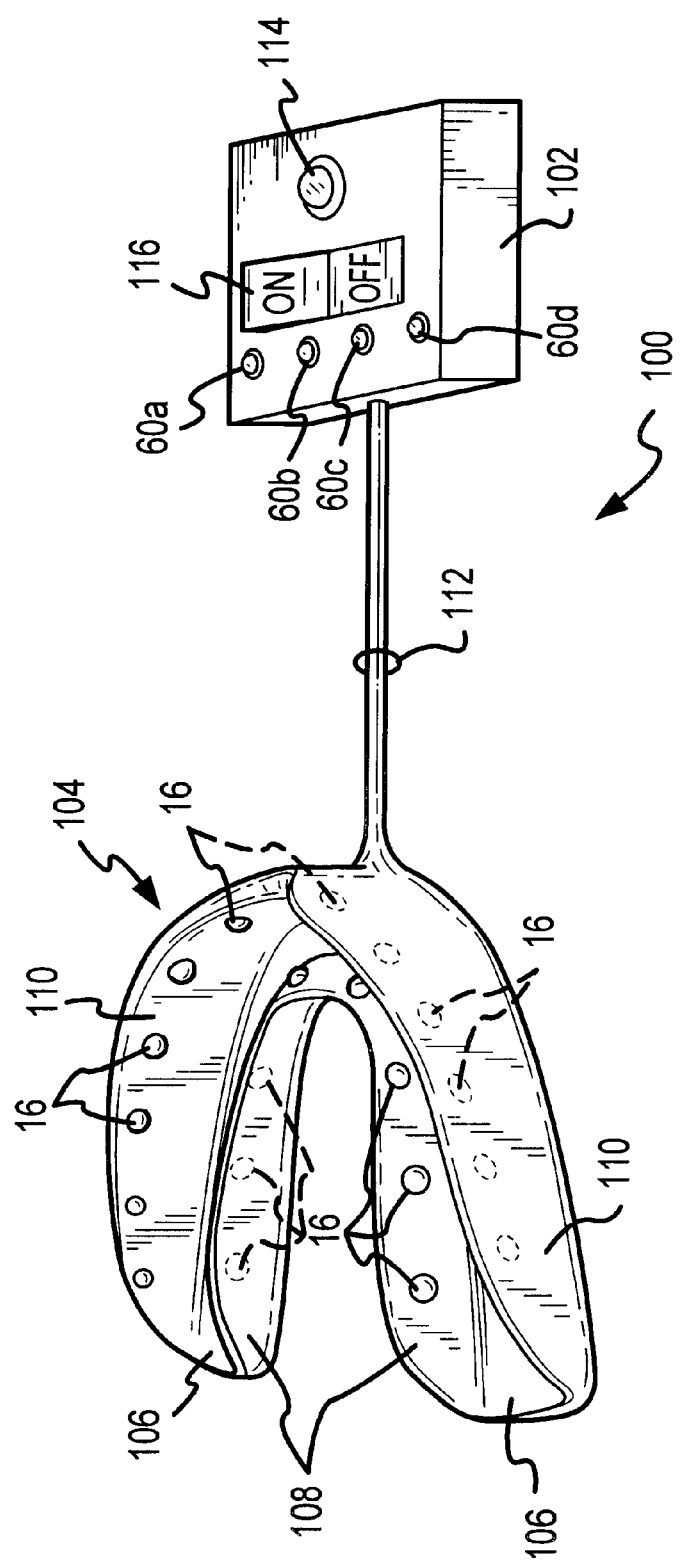
FIG. 3 is a perspective view of another embodiments of a photo-therapy or LLT device which incorporates the present invention and which is adapted to treat and facilitate the treatment of gum disease in the mouth of a human being.

The photo-therapy device 10 shown in FIG. 1 is suitable for external application to living tissue. The present invention can also be applied internally or can be adapted to treat specific areas and locations of living tissue by use of molds or positioning structures to locate the LEDs 16 at a specific location on the body, as is shown in FIG. 3 by another embodiment 100 of the photo therapy device. The photo therapy device 100 includes a housing 102 within which the components shown in FIGS. 2A and 2B are contained, other than the LEDs 16 and the thermistor 72.

The LEDs 16 and the thermistor 72 are positioned in a mouthpiece 104 which is intended to be placed within person's mouth over the teeth of the upper or lower dental arch. The teeth of the dental arch fit within a U-shaped or trough-like structure, which is formed in part by two oppositely positioned and spaced apart sidewalls 108 and 110 which extend upward (as shown) from a bottom wall 106. The LEDs 16 are embedded within the side walls 108 and 110, at locations which permit them to project light into the U-shaped trough-like structure, toward the opposite side wall 108 or 110. The thermistor 72 is embedded in the mouthpiece, at a location where the thermistor 72 can sense the temperature of the LEDs 16.

When the mouthpiece 104 is placed over the teeth, the positions of the LEDs 16 in the side walls 108 and 110 cause the emitted photo energy to impinge on the gums. The impinging photo energy therapeutically affects the gum tissue by promoting healthier gums, fighting infection and influences from bacteria, and by promoting healing of any gum tissue which has previously been injured. After photo therapeutically treating the gum tissue of either the upper or lower dental arch, the mouthpiece 104 is removed from the person's mouth, inverted, and placed over the other dental arch in a similar manner for the photo therapeutic treatment of the gum tissue of the other dental arch.

A cable 112 contains the conductors from the electronic components within the housing 102 to the LEDs 16 located and the thermistor 72 which are located in the mouthpiece 104. The LEDs 16 are preferably arranged in four groups comparable to four columns of LEDs shown in FIG. 2B. The LEDs of the inner sidewall 108 of one-half of the dental arch form one group, the LEDs on the inner sidewall of the other half of the dental arch form a second group, the LEDs on one-half of the outer sidewall 110 of the dental arch form a third group, and the LEDs on the other half of the outer sidewall 110 form the fourth group. For purposes of this description, the halves of the mouthpiece 104 occur at the location where the cable 112 connects to the mouthpiece. Although the four groups of LEDs 16 may be positioned as described, the LEDs can also be positioned in other configurations of groups in the mouthpiece 104. The conductors which connect to the LEDs 16 are embedded in the material of the mouthpiece.

An indicator LED 60a, 60b, 60c and 60d is connected in series with each group of LEDs located in the mouthpiece 104. Conductors in the cable 112 connect the indicator LEDs 60a, 60b, 60c and 60d to the photo therapeutic emitting LEDs 16. The indicator LEDs 60a, 60b, 60c and 60d in the housing 102 may be readily observed by the user as indicating the proper operation of each group of photo therapeutic LEDs 16 located in the mouthpiece 104. An indicator 114 is also present on the housing, to indicate the operation of the device 100. An on-off switch 116 controls the application of electrical power to the device 100. Preferably, the housing 102 may also contain battery or a connection to a conventional power terminal to obtain electrical power for operating the device 100. Although not shown, a connector may connect the end of the cable 112 to the housing 102, allowing the cable and the mouthpiece to be disconnected from the housing 102 for cleaning or sterilization between uses by different persons.

Preferably the material from which the mouthpiece 104 is made, and the material which surrounds the conductors in the cable 112 is of a flexible biocompatible plastic which will adapt and conform to different shapes of dental arches and which will not cause pain or irritation to the teeth or gum tissue when in contact with them. The electrical connections to the components in the mouthpiece 104 are insulated and isolated, so an electrical shock to the user will not occur.

As an alternative to the single mouthpiece 104 shown in FIG. 3, two mouthpieces could be employed to enable the treatment of the gum tissue on both the upper and lower dental arches simultaneously. The two mouthpieces would be formed separately or as a unitary structure. Each mouthpiece would have its own separate set of LEDs 16 positioned in the manner described above. Each of the two mouthpieces would have four groups of LEDs in the manner described above, and both mouthpieces would use collectively all eight of the columns of LEDs as shown in FIG. 2B. A single thermistor 72 would be used for sensing the temperature of both mouthpieces. The single thermistor 72 could accomplish its temperature sensing function when embedded in the unitary structure for both mouthpieces or when embedded in one of the two separate mouthpieces since the temperature of the two separate mouthpieces when used at the same time would essentially be the same within a person's mouth. The time required to treat both the gum tissue of both the upper and lower dental arches is reduced, because the upper and lower gum tissue could be treated simultaneously rather than sequentially.

In cases of the more rapid healing of gum tissue and insect bites, promoting healthier gum tissue, and relief from headache pain, the healing modality is thought to be the result of the infrared radiation interacting with the body tissues and substances to create an increased level of nitric oxide gas in the blood and tissue. Nitric oxide has been found to be a substantial antibacterial and antiviral agent. Nitric oxide signals the blood vessels and capillaries to dilate. The dilated blood vessels and capillaries increase the amount of blood circulation, which causes more healing at the location where the increased blood flow results, such as at the location of insect bites or in the gums. In the situation of relief from headache pain, the nitric oxide is believed to cause the capillaries in the brain to dilate which counteracts the effect of the headache, since the headache is generally regarded as being caused by constriction of capillaries. It is believed that this same dilation of vessels, capillaries, lymph vessels, and the like, as well as the production of nitric oxide, and the transfer of the thermal energy by the infrared radiation into deep locations within the body is responsible for the therapeutic benefits available from the present invention.

Many other advantages and improvements will be apparent to those having skill in the art, after gaining a complete understanding and comprehension of the present invention. Presently preferred embodiments of the invention and its improvements have been described with a degree of particularity. This description has been made by way of preferred example. It should be understood that the scope of the present invention is defined by the following claims, and should not be unnecessarily limited by the detailed description of the preferred embodiment set forth above.

The invention claimed is:

1. A photo-therapy device for supplying infrared radiation to tissue, comprising:

an emitter comprising an infrared light emitting diode operative to emit infrared radiation at a photo-therapeutic wavelength when current is conducted through the emitter, the emitter emitting infrared radiation at a wavelength related to a temperature of the emitter, the temperature of the emitter being related to the current conducted through the emitter;

a temperature regulation circuit including a temperature sensor disposed proximate to the emitter to sense the temperature of the emitter, the temperature regulation circuit supplying a control signal related to the temperature of the emitter sensed by the temperature sensor; and a controllable power supply connected to the emitter and responsive to the control signal to supply current to the emitter to cause the emitter to emit IR radiation and to establish and maintain a predetermined temperature of the emitter to result in the emission of infrared radiation at a predetermined wavelength.

2. A photo-therapy device as defined in claim 1, further comprising:

a plurality of emitters arranged in an array, the array having groups of at least one emitter per group;

a plurality of controllable switches, one controllable switch associated with each group, the controllable switch connected to conduct current through each emitter of the group with which the controllable switch is associated in response to an activation signal applied to that controllable switch; and a selector connected to each of the controllable switches and operative to supply an activation signal to each of the controllable switches to activate each of the controllable switches separately.

3. A photo-therapy device as defined in claim 2 wherein:

the selector supplies a separate activation signal to each of the controllable switches one at a time; and the emitters of each group of the array emit radiation simultaneously in response to the activation of the controllable switch associated with that group.

4. A photo-therapy device as defined in claim 3 wherein:

the selector supplies activation signals to each of the controllable switches in rotational sequence; and the groups of emitters in the array-emit radiation in rotational sequence in accordance with the activation of the controllable switches with which each group is associated.

5. A photo-therapy device as defined in claim 2 further comprising:

an indicator connected with each group of emitters and operative to supply a visible light signal upon the emitters of that group conducting current.

6. A photo-therapy device as defined in claim 5 wherein:

the indicator is a visible light emitting diode; and the infrared light emitting diodes and the visible light emitting diode are connected together in series in each group.

7. A photo-therapy device for supplying infrared radiation to tissue, comprising:

a plurality of emitters arranged in an array, the array having groups of at least one emitter per group, each emitter being operative to emit infrared radiation at a photo-therapeutic wavelength when current is conducted through the emitter, each emitter emitting infrared radiation at a wavelength related to a temperature of the emitter, the temperature of each emitter being related to the current conducted through the emitter;

a temperature regulation circuit including a temperature sensor disposed proximate to the emitters to sense the temperature of the emitters, the temperature regulation circuit supplying a control signal related to the temperature of the emitters sensed by the temperature sensor;

a controllable power supply connected to the emitters and responsive to the control signal to supply current to the emitters to cause the emitters to emit IR radiation and to establish and maintain a predetermined temperature of the emitters to result in the emission of infrared radiation at a predetermined wavelength;

a plurality of controllable switches, one controllable switch associated with each group, the controllable switch connected to conduct current through each emitter of the group with which the controllable switch is associated in response to an activation signal applied to that controllable switch;

a selector connected to each of the controllable switches and operative to supply an activation signal to each of the controllable switches to activate each of the controllable switches separately; and an indicator connected with each group of emitters and operative to supply a visible light signal upon the emitters of that group conducting current.

8. A photo-therapy device as defined in claim 2 wherein:
the controllable power supply applies an output voltage to the emitter;
the current conducted through the emitter is related to the output voltage applied to the emitter; and
changes in the control signal cause the controllable power supply to vary the output voltage applied to the emitter.

9. A photo-therapy device as defined in claim 8 wherein:
the emitter exhibits a characteristic increase in wavelength in response to an increase in temperature.

10. A photo-therapy device for supplying infrared radiation to tissue, the tissue having an optimal absorption wavelength, comprising:

an emitter operative to emit infrared radiation at a photo-therapeutic wavelength, the wavelength of the infrared radiation being related to a temperature of the emitter;

a temperature regulation circuit which senses the temperature of the emitter and generates a control signal related to the temperature; and a controllable power supply connected to the emitter and responsive to the control signal to apply an output voltage to the emitter, changes in the control signal cause the controllable power supply to vary the output voltage;

and wherein:
the tissue is under a skin of a patient;
the emitter has a characteristic wavelength of emitted radiation at room temperature which is shorter than the optimal absorption wavelength for the tissue, and
the temperature regulation circuit and the controllable power supply are operative to control and stabilize the temperature of the emitter at a predetermined temperature which results in an emitted radiation wavelength which is closer to the optimal tissue absorption wavelength than is the wavelength at room temperature.

11. A photo-therapy device as defined in claim 10 wherein:
the wavelength of the emitter at room temperature is approximately 880 nm.

12. A photo-therapeutic device as defined in claim 11 wherein:
the wavelength of the emitter at the predetermined temperature is approximately 884 nm.

13. A photo-therapy device as defined in claim 10 wherein:
the emitter comprises an infrared light emitting diode.

14. A photo-therapy device as defined in claim 13 wherein:
the infrared light emitting diode is a gallium aluminum arsenide light emitting diode.

15. A photo-therapy device for supplying infrared radiation to tissue, comprising:
a plurality of emitters arranged in groups of at least one emitter per group, each emitter operative to emit infrared radiation at a photo-therapeutic wavelength;

a temperature regulation circuit including a temperature sensor which senses the temperature of the emitters and supplies a control signal related to the sensed temperature;

a controllable power supply connected to the emitters and responsive to the control signal to supply current to the emitters to cause the emitters to emit IR radiation;

a plurality of controllable switches, one controllable switch associated with each group and connected to cause the current supplied by the controllable power supply to be conducted through each emitter of the group with which the controllable switch is associated in response to an activation signal applied to that controllable switch; and a selector connected to each of the controllable switches and operative to supply an activation signal to each of the controllable switches to activate each of the controllable switches separately;

and wherein:
the selector supplies activation signals to each of the controllable switches in rotational sequence; and
the groups of emitters emit radiation in rotational sequence in accordance with the activation of the controllable switches with which each group is associated.

16. A photo-therapy device as defined in claim 15 wherein:
the selector sequentially supplies activation signals to activate each of the controllable switches associated with each group to establish a radiation emitting duty cycle for each group of $1/n \times 100\%$, where n is equal to the number of groups.

17. A photo-therapy device as defined in claim 15 further comprising:
a current sensing element connected to each of the controllable switches through which the current conducted by the emitters of the groups flows when each controllable switch is activated.

18. A photo-therapy device as defined in claim 17 wherein the temperature regulation circuit further comprises:
a voltage divider network which includes the current sensing element, the voltage divider network deriving the control signal relative to a voltage across the current sensing element caused by current conducted through the group of emitters and through the current sensing element.

19. A photo-therapy device as defined in claim 18 wherein:
the voltage divider network further includes the temperature sensor; and
the control signal is additionally derived relative to a voltage across the temperature sensor caused by a current flowing through the temperature sensor.

20. A photo-therapy device as defined in claim 19 wherein:
each emitter has a characteristic in which an increase in temperature causes a decrease in resistance of the emitter.

21. A photo-therapy device as defined in claim 15 wherein:
the controllable power supply applies an output voltage to each group of emitters; and
the control signal is further derived in relation to the output voltage of the controllable power supply using a voltage divider network.

22. A photo-therapy device as defined in claim 21 wherein:
the voltage divider network further includes a device exhibiting a fixed voltage reference;
the control signal is further derived relative to the fixed voltage reference with respect to the output voltage of the controllable power supply.

23. A photo-therapy device as defined in claim 21 wherein:
the temperature sensor has a resistance which varies in a predetermined manner relative to the temperature of the temperature sensor, the temperature sensor exhibiting a temperature-related voltage developed by current flowing through the resistance of the temperature sensor; and
the voltage divider network derives the control signal relative to the temperature-related voltage across the temperature sensor and the voltage across a current sensing element caused by current flowing through the group of emitters, when current flows through the emitters of each group.

24. A photo-therapy device as defined in claim 23 wherein:
the voltage divider network further includes a device exhibiting a fixed voltage reference; and
the control signal is further derived relative to the output voltage of the controllable power supply from which the fixed voltage reference has been subtracted, when current does not flow through the emitters of each group.

25. A photo-therapy device as defined in claim 24 wherein:
the selector supplies the activation signals to selectively cause only one of the plurality of controllable switches to be conductive at any given time as all of the controllable switches are selected to be activated in rotational sequence.

26. A photo-therapy device as defined in claim 15 wherein the selector further comprises:
an oscillator supplying a clock signal having a clock frequency; and
a decoder connected to the oscillator and having a plurality of output terminals each of which is connected to a different controllable switch connected to the emitters of the group with which the controllable switch is associated, the decoder responding to the clock signal to supply the activation signal on one of the output terminals with each cycle of the clock signal.

27. A photo-therapy device for supplying infrared radiation to tissue, comprising:
an emitter operative to emit infrared radiation at a photo-therapeutic wavelength related to a temperature of the emitter;
a temperature regulation circuit which senses the temperature of the emitter and supplies a control signal related to the sensed temperature; and
a controllable power supply connected to the emitter and responsive to the control signal to apply an output voltage to the emitter to cause the emitter to emit the IR radiation, changes in the value of the control signal cause the controllable power supply to vary the output voltage applied to the emitter;
and wherein:
the controllable power supply receives an input voltage within a range of input voltages; and
the controllable power supply generates the output voltage at a value established by the control signal substantially independent of the input voltage within the range of input voltages.

28. A photo-therapy device as defined in claim 27 wherein:
the controllable power supply comprises a switching power supply.

29. A photo-therapy device as defined in claim 27 wherein:
the controllable power supply comprises a boost type switching power supply.

30. A photo-therapy device as defined in claim 29 wherein the boost type switching power supply further comprises:
an inductor electrically connected at a first terminal to an input voltage supply;
a filter capacitor connected via a diode at a second terminal of the inductor;
a controllable switch connected at the second terminal of the inductor to conduct current through the inductor from the input voltage supply; and
a switching regulator connected to the controllable switch to selectively control the conduction of the controllable switch relative to a voltage across the filter capacitor.

31. A photo-therapy device as defined in claim 30 wherein:
the temperature regulation circuit further comprises a voltage divider network connected to receive the output voltage from the controllable power supply to derive the control signal relative to the output voltage from the controllable power supply;
the control signal is applied to the switching regulator; and
the switching regulator responds to the control signal to vary a time interval of conduction of the controllable switch relative to a time interval of non-conduction of the controllable switch.

32. A photo-therapy device for supplying infrared radiation to tissue, comprising:
a plurality of emitters arranged in an array, the array having groups of at least one emitter per group, each emitter emitting infrared radiation at a photo-therapeutic wavelength when current is conducted through the emitter;
a plurality of controllable switches, one controllable switch associated with each group, the controllable switch connected to conduct current through each emitter of the group with which the controllable switch is associated in response to an activation signal applied to that controllable switch;
a selector connected to each of the controllable switches and operative to supply an activation signal to each of the controllable switches to activate separately each of the controllable switches;
a controllable power supply connected to the array and operative to apply a controllable level of output voltage to the array, the level of the output voltage establishing an amount of current flow through the emitters, the controllable power supply responding to a control signal to vary the level of output voltage; and
a voltage sensing network connected to the array to sense the output voltage from the controllable power supply and to supply a control signal to the controllable power supply which is related to the output voltage.

33. A photo-therapy device as defined in claim 32 wherein:

each controllable switch is associated with a group of emitters in the array;

the selector supplies activation signals to each of the controllable switches in rotational sequence;

the groups of emitters emit radiation in rotational sequence in accordance with the activation of the controllable switches with which each group is associated; and further comprising:

a current sensing element connected to each of the controllable switches and through which the current conducted by the emitters of the groups flows when each each controllable switch is activated.

34. A photo-therapy device as defined in claim 33 wherein:

the current sensing element develops a voltage thereacross related to the amount of current conducted through the current sensing element; and the voltage sensing network comprises a voltage divider network which includes the current sensing element.

35. A photo-therapy device as defined in claim 34 wherein:

the voltage divider network further comprises a device exhibiting a fixed voltage reference; and the control signal is further derived relative to the output voltage of the controllable power supply from which the fixed voltage reference has been subtracted when current is not conducted through the emitters of each group by the controllable switch.

36. A photo-therapy device as defined in claim 34 wherein:

the voltage divider network further includes a temperature sensor disposed proximate to at least one emitter of the array to sense the temperature of the emitters of the array, the temperature sensor establishing a resistance related to the temperature sensed.

37. A photo-therapy device for supplying infrared radiation to tissue, comprising:

at least one emitter emitting infrared radiation at a photo-therapeutic wavelength when current is conducted through the emitter, the amount of current conducted through the emitter depending upon a characteristic resistance of the emitter and a level voltage applied to the emitter; and a boost type switching power supply connected to the one emitter and operative to apply an output voltage to the emitter, the boost type switching power supply comprising:

an inductor electrically connected at a first terminal to an input voltage supply;

a filter capacitor connected via a diode at a second terminal of the inductor;

a controllable switch connected at the second terminal of the inductor to conduct current through the inductor from the input voltage supply;

a switching regulator connected to the controllable switch and responsive to a control signal to selectively control a conduction time and a non-conduction time of the controllable switch; and a voltage sensing network connected to the emitter to sense the output voltage from the switching power supply and to derive the control signal for controlling the switching regulator which is related to the output voltage and a temperature of the emitter.

38. A method for generating photo-therapeutic radiation for treating a condition of a living tissue, comprising the steps of:

providing a voltage supply;

emitting photo-therapeutic radiation from an emitter in response to current flow through the emitter from the voltage supply;

generating a temperature signal relative to a temperature of the emitter; and regulating the voltage supply in response to the temperature signal.

39. A method for generating photo-therapeutic radiation for treating a condition of a living tissue, comprising the steps of:

emitting photo-therapeutic radiation from a plurality of emitters in response to current flow through the plurality of emitters from a voltage supply, the plurality of emitters arranged in an array, the array having groups of at least one emitter per each group;

conducting current through each emitter of the group separately in rotational sequence through all the groups; and regulating a voltage from the voltage supply applied to the array of emitters to control the current conducted through each group of emitter in the rotational sequence.

40. A method of therapeutically enhancing natural healing of insect bites in human tissue comprising:

placing an infrared source in close proximity to the tissue at a location of the insect bite;

applying infrared light energy from the infrared source to the tissue at the location of the insect bite.

41. A method of photo therapeutically treating gum tissue of a human being with a mouthpiece adapted to fit within the human being's mouth over the human being's teeth, the mouthpiece having a plurality of infrared light emitters arranged in facing sets comprising:

positioning the mouthpiece within the human being's mouth with the teeth and gum tissue between the facing sets of infrared light emitters; and applying infrared light energy to the gum tissue from the infrared light emitters located within the mouth of the human being.

* * * * *